United States Patent
Hässig et al.

[11] Patent Number: 6,136,037
[45] Date of Patent: Oct. 24, 2000

[54] IMPLANT DELIVERY DEVICE IN THE TREATMENT OF TROCHANTER AND SUBTROCHANTER FRACTURES

[75] Inventors: Christoph Hässig, Oberentfelden; Christian Habegger, Schoftland; Hans Schmotzer, Kölliken, all of Switzerland

[73] Assignee: Intraplant AG, Cham, Switzerland

[21] Appl. No.: 09/355,717

[22] PCT Filed: Feb. 2, 1998

[86] PCT No.: PCT/EP98/00546

§ 371 Date: Nov. 22, 1999

§ 102(e) Date: Nov. 22, 1999

[87] PCT Pub. No.: WO98/33442

PCT Pub. Date: Aug. 6, 1998

[30] Foreign Application Priority Data

Feb. 3, 1997 [DE] Germany ............ 197 03 987

[51] Int. Cl.[7] .................................................. A61F 2/36
[52] U.S. Cl. ................................. 623/23.11; 623/23.15
[58] Field of Search ........................... 623/23.11, 23.12, 623/23.14, 23.15, 23.26; 606/61, 62, 63, 64, 65, 66, 67, 68, 69, 96, 97, 102

[56] References Cited

U.S. PATENT DOCUMENTS 4,976,713  12/1990  Landanger et al. ............ 60/62
5,334,192  8/1994  Behrens ....................... 606/96
5,941,879  8/1999  Walulik et al. ................ 606/61

FOREIGN PATENT DOCUMENTS 496950   10/1996  European Pat. Off. ........... 623/23.11
736286   10/1996  European Pat. Off. ........... 623/23.11
2647006  11/1990  France ......................... 623/23.11

*Primary Examiner*—Pedro Philogene
*Attorney, Agent, or Firm*—Knobbe, Martens, Olson & Bear, LLP

[57] ABSTRACT

Aiming device for an implant to attend trochanter and subtrochanter fractures, comprising a head for connecting a famur pin and with an aiming arm (10) mounted laterally on the head which extends approximately -arallel to the femur pin and at least two slanted aiming passages (12, 13) aligned to proximal slanted passages of the femur pin for a shank neck blade or the like, and at least two transverse aiming bores aligned to distal transverse bores of the femur pin for accommodating a strike-in sleeve and/or bore sleeve. The slanted aiming passages (12, 13) include different angles relative to the aiming arm axis (11). The longitudinal axes of the slanted aiming passages (12, 13) further cross the longitudinal axes of the transverse aiming bores (21, 22). The aiming arm (10) and head for connection of the femur pin are detachable joined together. The transverse aiming bores (21, 22) are part of a plateshaped insert element (insert plate 20) which is placeable and fixable within a corresponding passage (19) in the airming arm (10).

12 Claims, 3 Drawing Sheets

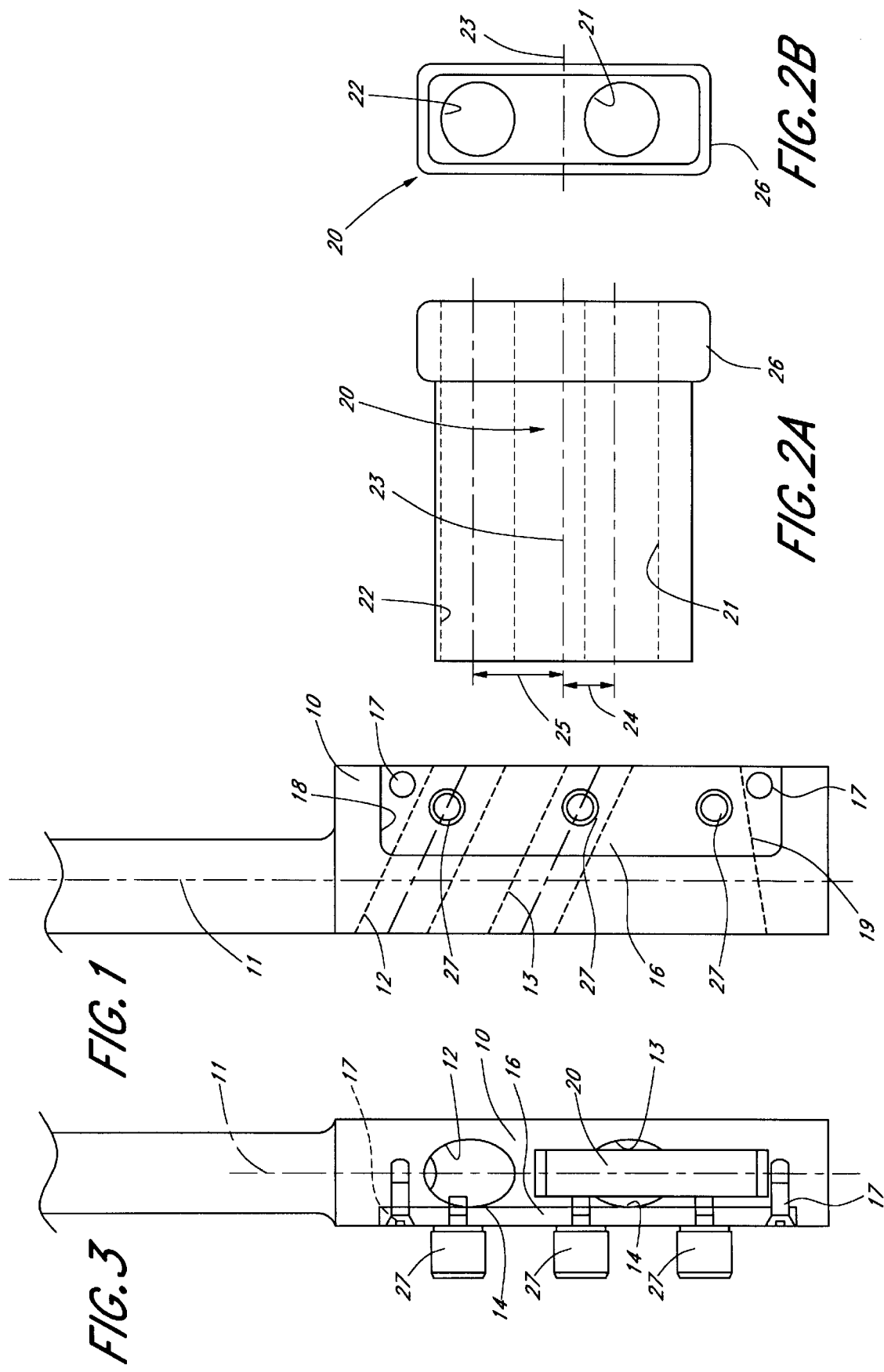

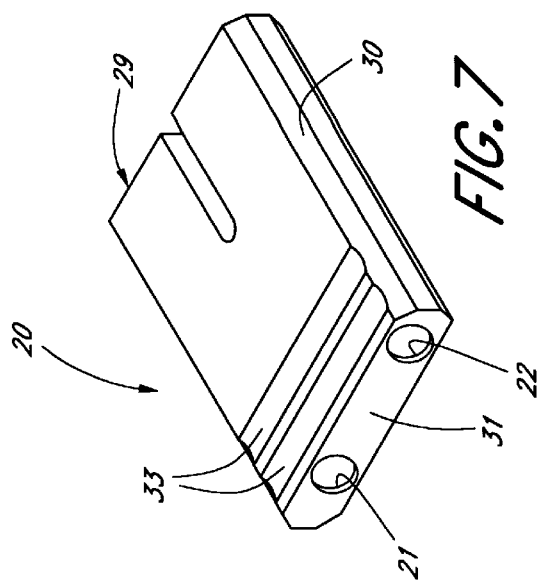
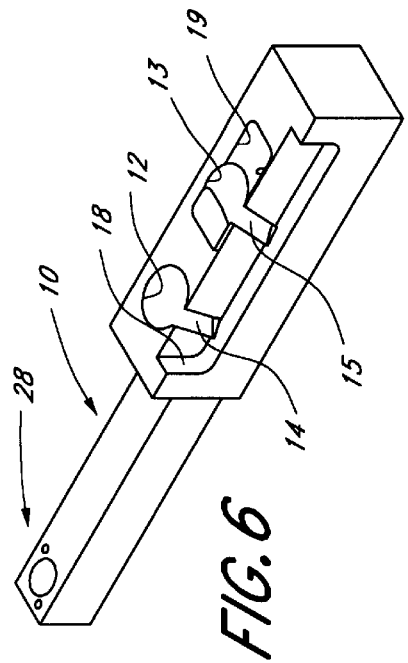
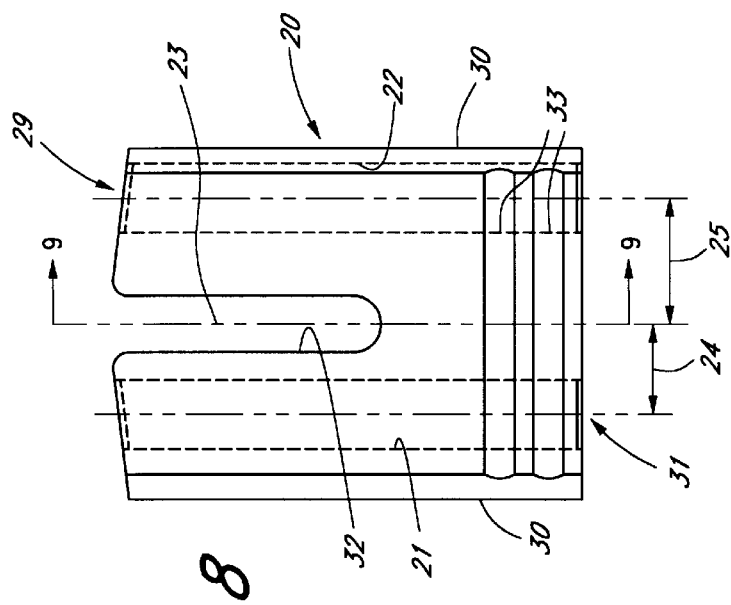
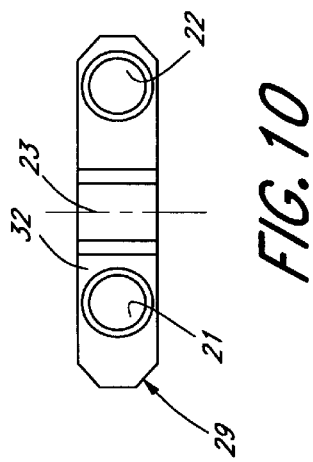
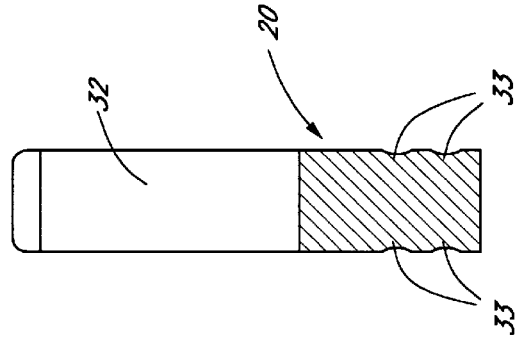

IMPLANT DELIVERY DEVICE IN THE TREATMENT OF TROCHANTER AND SUBTROCHANTER FRACTURES

FIELD OF THE INVENTION

The invention relates to an aiming device for an implant to attend trochanter and subtrochanter fractures.

BACKGROUND OF THE INVENTION

From the EP 0 496 950 B1 is known an aiming device for an implant to attend trochanter and subtrochanter fractures comprising a head with a pin for holding a femur pin which is inserted into the marrow area. Furthermore, this aiming device comprises an aiming arm, which is mounted laterally on the head and extends approximately parallel to the femur pin and comprises at least two slanted aiming bores aligned to proximal slanted bores of the femur pin for a shank neck screw and at least one transverse aiming bore aligned with a distal transverse bore of the femur pin for a distal locking screw for accomodating a bore sleeve. The head is in its conventional form of embodiment undetachably mounted on the aiming arm. Furthermore, the head comprises arresting means for detachable mounting as well as a striking surface for driving in the femur pin. The aiming arm comprises a plurality of slanted aiming bores which are at different angles relative to the aiming arm axis and are at least partially crossed by the transverse aiming bore. This design allows accommodation of all aiming bores in a relatively short section of the aiming device, so that the aiming device can be of respective compact construction.

A disadvantage of the known design lies in the rigid association of all aiming bores relative to each other. In particular, the known aiming device does not allow in particular matching of transverse aiming bores to different distal transverse bores of the femur pin. It has to be taken into consideration that modern femur pins have elongated transverse bores in the distal area in order to be either statically or dynamically locked. The known aiming device is unsuitable for this due to the static association of the aiming bores relative to each other.

SUMMARY OF THE INVENTION

It is an object of the present invention to offer an aiming device of the aforedescribed type which has more degrees of freedom relative to the transverse aiming bores.

This object is achieved according to the invention by an aiming device having a head for joining a femur pin, an aiming arm, and a plateshaped insert element. The aiming arm is mounted laterally to the head and extends approximately parallel to the femur pin. The aiming arm has at least two slanted aiming passages aligned to a proximal slanted passage of the femur pin for one of a shank element, and at least two transverse bores aligned to a distal transverse bore of the femur pin to accommodate a sleeve. The slanted aiming passages include different angles relative to an axis of the aiming arm, and longitudinal axes of the slanted aiming passages cross the longitudinal axes of the transverse aiming bores. The plateshaped insert element is placeable and fixable within a corresponding passage in the aiming arm, and has a longitudinal center axis. The transverse aiming bores are part of the insert element and extend parallel to the longitudinal center axis, at a variant distance therefrom so that the transverse aiming bores are displaceable by turning the insert plate by 180 degrees.

The inventive design distinguishes itself for one in that it can be of extremely compact design, and for this purpose at least the distal slanted aiming passage in the aiming arm intersects with the passage for the plateshaped insert element or the insert plate in which the transverse aiming bores are established. The variability of the inventive aiming device is obtained in that insert plates of differently directed and/or differently dimensioned and/or differently spaced transverse bores are made available. The transverse aiming bores of an insert plate may extend either parallel to each other or at an angle to each other.

Particularly advantageous is the form of embodiment, according to which the transverse aiming bores extend parallel to the longitudinal centre axis of the insert plate but at a different distance therefrom. This makes it possible to set the transverse aiming bores either a little further upwards or a little further downwards by way of turning the insert plate by 180 degrees, so that with forming elongated transverse bores in the distal area of an associated femur pin both a static or dynamic anchorate of the latter is possible.

The slanted aiming passages, which are aligned to corresponding proximal slanted passages of the femur pin, serve to accommodate a strike-in sleeve and/or a bore sleeve. A strike-in sleeve is always used if the shank neck stabilisation element is a shank neck blade which is struck but not screwed into the shank neck bone, as is suggested in the prior art.

The slanted aiming passages preferably comprise at least over part of their length a respective asymmetrical cross-section, in particular a circular cross-section flatted on at least one side, so that a strike-in sleeve can be non-rotationally placed. The flattening of the slanted aiming passages is obtained in a special form of embodiment in that a respective bore in the aiming arm is designed to be open on at least one side over a specified length, and this opening is sealable by a plane surface plate. The strike-in sleeve is then of a corresponding respectively complementary designed contour in the direction transversely to the longitudinal extent. The aforementioned shank neck blade can be driven through the strike-in sleeve into the shank neck bone.

One embodiment of the aiming device according to which the end surface of the insert plate which is facing the femur pin is rooflike slanted from its longitudinal centre axis in the respective direction of the two narrow longitudinal sides, serves to prevent collisions between the insert plate and the femur. It has to be taken into consideration that the insert plate is designed to be longer than the corresponding passage in the aiming arm, so that the insert plate protrudes at the side of the femur over the aiming arm, i.e. at an angle deviating from 90 degrees relative to the aiming arm axis. The angle of the rooflike slant relative to the longitudinal centre axis of the insert plate corresponds preferably with the angle between the aiming arm axis and the longitudinal centre axis of the passage for the insert plate in the aiming arm.

Other embodiments serve, with eccentric arrangement of the transverse aiming bores relative to the longitudinal centre axis of the insert plate, instantaneous recognition of the eccentricity of these transverse aiming bores.

Another embodiment provides for an operationally safe fixing of the insert plate within the associated passage in the aiming arm.

It is understood that the slanted aiming passages 12, 13 can be circular bores or oval bores, so that the sealing plate 16 can be dispensed with. In this case, aiming arm 10 is formed in one piece.

BRIEF DESCRIPTION OF THE DRAWINGS

Further features and advantages of the inventive aiming device will now be described in more detail, based on an exemplary embodiment which is diagrammatically illustrated in the enclosed drawing. Shown are, in FIG. 1 a section, i.e. the distal section, of an aiming arm according to the invention, in a diagrammatical side view;

FIGS. 2a and 2b a first form of embodiment of an inventive insert plate, here an eccenter plate, in a side view, end view and perspective view;

FIG. 3 the distal area of the aiming arm illustrated in FIG. 1, in a top lateral view;

FIG. 6 the aiming arm as in FIGS. 4 and 5, in a perspective view;

FIGS. 8–10 a second form of embodiment of an inventive insert plate, i.e. an eccenter plate, in a flat side view, perspective view, cross-sectionally along longitudinal line A—A, and endsided view.

DETAILED DESCRIPTION OF THE INVENTION

Figure 4:
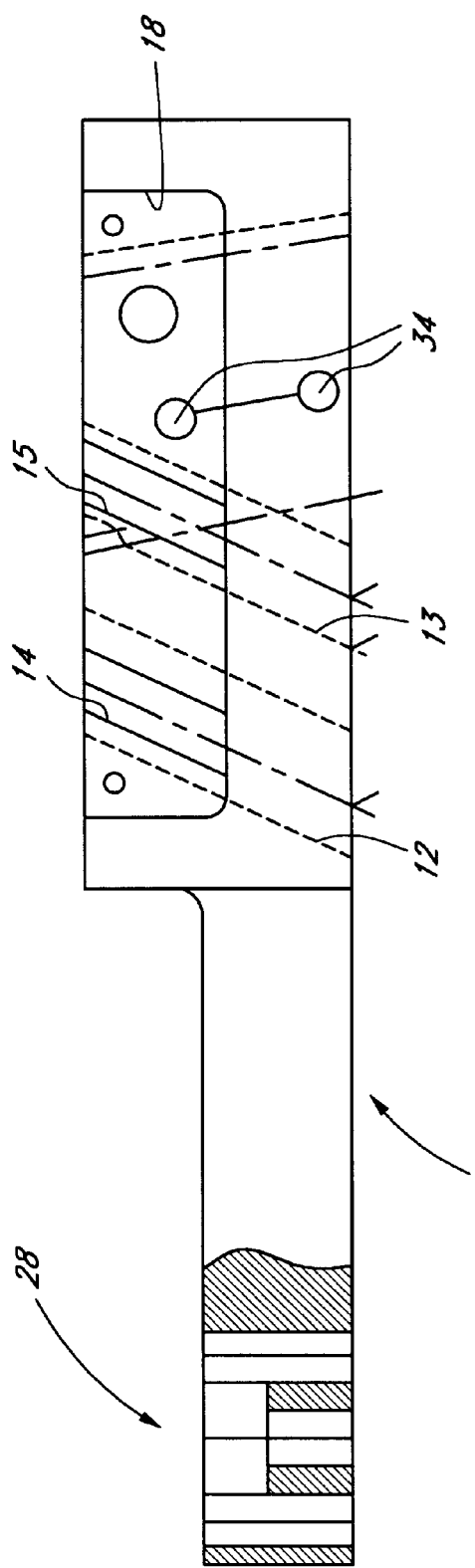
FIG. 4 a second form of embodiment of an inventive aiming arm in a diagrammatical side view.

In FIGS. 1 and 3 is illustrated, in a side view and a front view, the distal section of an aiming arm 10 which is detachably joined to a head in the proximal area. A femur pin is connectable to this head. The aforementioned head and the connection with a femur pin are conventional operations, so that an explanation can be dispensed with. However, it maybe mentioned that the detachable connection between head and aiming arm is advantageously such that both parts are made of different materials, for example the head of plasted. This structure and the two-part design offer respective X-ray technical advantages. The X-ray image is not interfered with by the plastic aiming arm. Mounting the aiming arm 10 on the aforementioned head is carried out in such a manner that longitudinal axis 11 of the aiming arm extends approximately parallel to a femur pin which is mountable on the head.

In aiming arm 10 are established first aiming passages 12, 13 which include different angles relative to the aiming arm axis 11 of preferably 125 degrees, 130 degrees or 135 degrees. Also feasible is an angle of 140 degrees. In the present case, two slanted aiming passages 12, 13 are provided. It is also feasible to provide more than two slanted aiming passages. These slanted aiming passages serve to accommodate a strike-in sleeve (not illustrated in detail) for striking in of a cross-sectionally contoured shank neck stabilisation element, in particular a shank neck blade with double-T-cross-sectional profile, star profile, T-profile or the like. The respective slanted aiming passage is selected according to the alignment of a proximal slanted passage in the femur pin selected by anatomical conditions. Both slanted aiming passages 12 and 13 comprise at least of part of their length (see in particular FIG. 6) a respective asymmetrical circular cross-section, i.e. flattened on one side, for non-rotary placement of the aforementioned strike-in sleeve the outside contour of which corresponds with the aforementioned cross-section of the aiming passages 12 and 13. Flattening of slanted aiming passages 12, 13 is obtained in that a corresponding bore is set in aiming arm 10 in such a manner that it can be of open design on at least one side, the left side in FIG. 3, over a predetermined length (see FIG. 6), and this opening 14, 15 is sealable by a plane surface plate 16. Plate 16 is fixed on aiming arm 10, i.e. with a corresponding cutout 18. Fixing within cutout 18 is such that plate 16 is externally flush with aiming arm 10.

Furthermore, aiming arm 9 has a second passage 19 which is according to FIG. 1 also slanted towards aiming arm longitudinal axis 11, i.e. in opposition to the slant of the first slanted aiming passages 12 and 13. Passage 19 is arranged in such a manner that it crosses or cuttingly passes through the distal slanted aiming passage 13. The slanted passage 19 serves to accommodate a plateshaped insert part or an insert plate 20, which includes transverse aiming bores 21, 22 which extend parallel to the longitudinal axis of the insert plate 20, which are in a mounted state of insert plate 20 oriented towards distal transverse bores of the femur pin (not illustrated). As a rule, each femur pin has two distal transverse bores, and modern femur pins have elongated transverse bores so that the femur pin can be fixed either statically or dynamically in the femur. In the case of static fixing, the bone screws abut the proximal end of the elongated transverse bores, whereas in the case of dynamic fixing, they abut the distal end of the aforementioned elongated transverse bores. In order to facilitate corresponding placement of the bone screw, the transverse aim bores 21, 22 are relative to the longitudinal centre axis 23 of insert plate 20 differently spaced from longitudinal centre axis 23. By turning insert plate 20 by 180 degrees, transverse aiming bores 21, 22 can be displaced from the bottom to the top and vice versa. The different distances of the longitudinal axes of the transverse aiming bores 21, 22 from longitudinal centre axis 23 of insert plate 20 is illustrated in FIG. 2a by distance arrows 24, 25. An insert plate of this type can thus also be described as an eccentric plate as transverse aiming bores 21, 22 are arranged eccentrically relative to longitudinal centre axis 23.

Insert plate 20 is at its lateral end surface provided with an outwardly protruding collar 26 in order to prevent excessive pushing of insert plate 20 from the lateral into slanted passage 19 of aiming arm 10. This collar serves as a stop on the lateral side of aiming arm 10 during lateral insertion of insert plate 20 into passage 19 of aiming arm.

Once insert plate 20 has been mounted, only the proximal slanted passage 12 is accessible. Insert plate 20 is to be removed if distal slanted aiming passage 13 is to be used.

The advantage of insert plate 20 lies in that one, two, three or more transverse aiming bores can be established therein in parallel or at an angle to each other. It is also feasible to make available insert plates with transverse aiming bores of different diameters. It is also possible to make available insert plates with transverse aiming bores which are at a different distance from longitudinal centre axis 23 of insert plate 20. Furthermore, the variability of the described construction is considerably improved by comparison to the rigid design according to the aforementioned prior art.

In the form of embodiment of FIGS. 1 to 3, insert plate 20 is fixed by clamping screws 27 which are screwed into corresponding threaded bores of plate 16. Slanted aiming passages 12 and 13 are also associated with clamping screws corresponding with clamping screws 27, as can be seen in particular in FIG. 1. In this respect, central clamping screw 27 of FIG. 1 serves a double function. It serves, on the one hand, to clamp insert plate 20 and, on the other hand, to clamp a strike-in sleeve which is inserted into the distal slanted aiming passage 13.

Figure 5:
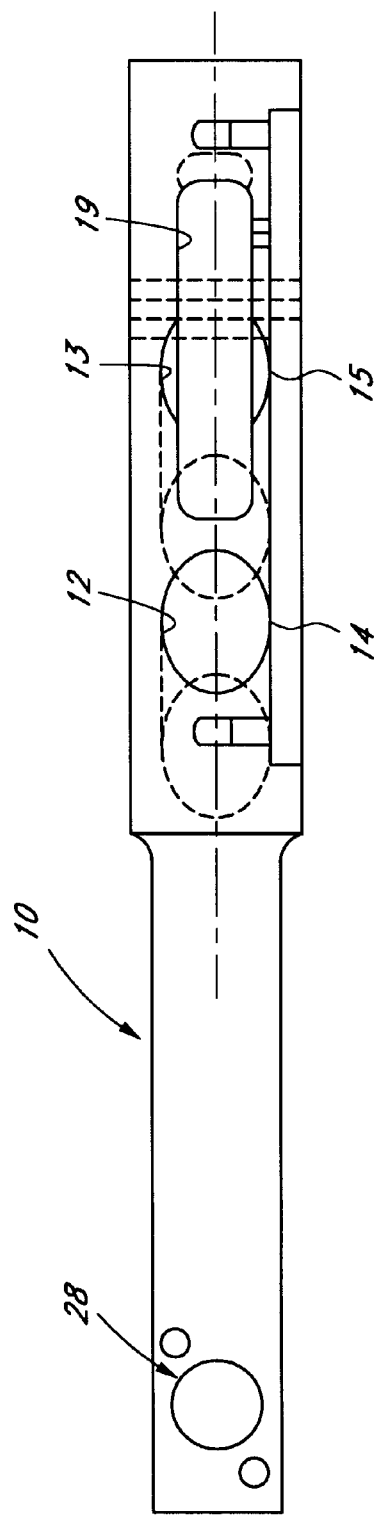
FIG. 5 the aiming arm as in FIG. 4 in a lateral top view.

The form of embodiment according to FIGS. 4 to 6 corresponds essentially of that of FIGS. 1 to 3, and FIG. 6 very nicely shows the longitudinal openings of the slanted aiming passages 12 and 13 which are then sealed by the aforementioned plate 16. Furthermore, FIGS. 4 to 6 show the proximal end of aiming arm 10 with a device 28 for connecting the aforementioned head. Furthermore, FIG. 6 clearly shows intersections between passage 19 on the one hand and distal slanted aiming passage 13.

In the form of embodiment according to FIGS. 4 to 6, the longitudinal edges of passage 19 are rounded off. Insert plate 20 will then of course also have to have rounded or phased longitudinal edges.

The insert plate associated with form of embodiment according to FIGS. 4 to 6 is illustrated in FIGS. 7 to 10. It is again denoted 20. The transverse aiming bores are denoted 21, 22. The longitudinal centre axis of insert plate 20 is also shown in FIGS. 8 and 10 under reference number 23. Transverse aiming bores 21, 22 are, relative to longitudinal centre axis 23 of insert plate 20, at different distances from longitudinal centre axis 23. The respective distance arrows are here again denoted 24 and 25.

In the form of embodiment illustrated in FIGS. 7 to 10, end surface 29 of insert plate 20 facing towards the femur pin is commencing from longitudinal centre axis 23 rooflike slanted in the direction of both narrow longitudinal sides 30, i.e. in the lateral direction. Thus, a collision of the inner end with the patient can be avoided in spite of the slanted application of insert plate 29. The angle of the rooflike slant relative to the longitudinal centre axis corresponds approximately with the angle of the longitudinal centre axis of passage 19 relative to longitudinal axis 11 of aiming arm 10.

Furthermore, in the form of embodiment of FIGS. 7 to 10, insert plate 20 has, starting from end surface 29 in direction of end surface 31 which is facing away from the femur pin, a cut or longitudinal slot 32 which extends in the direction of longitudinal centre axis 23, i.e. over approximately ⅔ of the total length of insert plate 20. This longitudinal slot corresponds during insertion of insert plate 20 into aiming arm passage 19 with guide pins 34 which extends through it. They are spaced in series in the insert direction or in the direction parallel to the longitudinal axis of passage 19. They hold the insert plate playfree in the passage and simplify insertion and extraction of the insert plate without danger of jamming during insertion or extraction.

At the lateral end, insert plate 20 is provided on at least one, here both, flat sides with grabbing grooves 33 or grabbing moulds of this type or grabbing aids which simplify handling. Fixing insert plate 20 in passage 19 is carrier out by the aforementioned clamping screws 27.

All features revealed in the application documents are claimed as essential parts of the invention inasmuch as they are individually or in combination new relative to the prior art.

List of Reference Marks
10 Aiming Arm
11 Longitudinal Axis of Aiming Arm
12 Slanted Aiming Passage
13 Slanted Aiming Passage
14 Opening
15 Opening
16 Plate
17 Screws
18 Cutout
19 Slanted Passage
20 Insert Plate
21 Transverse Aiming Bore
22 Transverse Aiming Bore
23 Longitudinal Centre Axis
24 Distance Arrow
25 Distance Arrow
26 Peripheral Collar
27 Clamping Screw
28 Head Connecting Mechanism
29 End Surface
30 Longitudinal Side (small)
31 End Surface
32 Longitudinal Slot
33 Grabbing Grooves
34 Guide Pins

What is claimed is:

1. An aiming device for an implant to attend trochanter and subtrochanter fractures, comprising:
    a head for joining a femur pin;
    an aiming arm mounted laterally to the head, the aiming arm extending approximately parallel to the femur pin, and comprising at least two slanted aiming passages aligned to a proximal slanted passage of the femur pin for a shank element, and at least two transverse bores aligned to a distal transverse bore of the femur pin to accommodate a sleeve, the slanted aiming passages including different angles relative to an axis of the aiming arm, and longitudinal axes of the slanted aiming passages crossing the longitudinal axes of the transverse aiming bores; and
    a plateshaped insert element which is placeable and fixable within a corresponding passage in the aiming arm and has a longitudinal center axis, the transverse aiming bores being part of the insert element and extending parallel to the longitudinal center axis, at a variant distance therefrom so that the transverse aiming bores are displaceable by turning the insert plate by 180 degrees.

2. The aiming device of claim 1, wherein the sleeve includes at least one of a strike-in sleeve and a bore sleeve.

3. The aiming device of claim 1, wherein the shank element includes one of a neck blade and a neck stabilisation element.

4. The aiming device of claim 1, wherein an end surface of the insert plate facing towards the femur pin is rooflike slanted, starting from the longitudinal center axis in a respective direction of both narrow longitudinal sides.

5. The aiming device of claim 4, wherein the insert plate comprises a longitudinal slot starting from the end surface facing towards the femur pin in the direction of the end surface facing away from the femur pin, which corresponds with a guide element for the insert plate arranged in the passage for insert plate.

6. The aiming device of claim 5, wherein the longitudinal slot extends in a direction of the longitudinal center axis of the insert plate.

7. The aiming device of claim 5, wherein the longitudinal slot has a length which is between about ½ and about ⅔ of a total length of the insert plate.

8. The aiming device of claim 1, wherein the insert plate is fixed by at least one clamping screw which is screwed into the aiming arm.

9. The aiming device of claim 1, wherein the aiming arm and the head are detachably joined together for connection of the femur pin.

10. The aiming device of claim 1, wherein respective slanted aiming passages comprise at least over a part of their lengths asymmetrical cross-sections for rotary placement of a sleeve.

11. The aiming device of claim 10, wherein the asymmetrical cross-section is a circular cross-section flattened on at least one side.

12. The aiming device of claim 11, wherein flattening of the slanted aiming passages is obtained by a respective bore in the aiming arm configured to be open on at least one side over a predetermined length to form an opening that is scalable by a plane surface plate.

* * * * *